US010874462B2

(12) United States Patent
Govari et al.

(10) Patent No.: US 10,874,462 B2
(45) Date of Patent: Dec. 29, 2020

(54) NETWORK SNIFFER FOR SYSTEM WATCHDOG AND DIAGNOSTIC

(71) Applicant: Biosense Webster (Israel) Ltd., Yokneam (IL)

(72) Inventors: Assaf Govari, Haifa (IL); Oleg Khudish, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 550 days.

(21) Appl. No.: 15/638,690

(22) Filed: Jun. 30, 2017

(65) Prior Publication Data

US 2019/0000557 A1 Jan. 3, 2019

(51) Int. Cl.
| | |
|---|---|
| *H04L 12/26* | (2006.01) |
| *A61B 34/20* | (2016.01) |
| *A61B 18/14* | (2006.01) |
| *A61B 18/18* | (2006.01) |
| *A61B 17/00* | (2006.01) |
| *A61B 18/00* | (2006.01) |

(Continued)

(52) U.S. Cl.
CPC .......... *A61B 34/20* (2016.02); *A61B 18/1492* (2013.01); *A61B 18/18* (2013.01); *H04L 43/04* (2013.01); *H04L 43/0811* (2013.01); *H04L 43/0823* (2013.01); *A61B 5/042* (2013.01); *A61B 5/062* (2013.01); *A61B 2017/00017* (2013.01); *A61B 2017/00022* (2013.01); *A61B 2018/00005* (2013.01); *A61B 2018/0016* (2013.01); *A61B 2018/00071* (2013.01); *A61B 2018/00351* (2013.01); *A61B 2018/1861* (2013.01)

(58) Field of Classification Search
CPC ..... A61B 34/20; A61B 18/1492; A61B 18/18; A61B 2017/00017; A61B 2017/00022; A61B 2018/1861; H04L 43/04; H04L 43/0811; H04L 43/0823
See application file for complete search history.

(56) References Cited

U.S. PATENT DOCUMENTS

| | | | |
|---|---|---|---|
| 5,012,814 A | * | 5/1991 | Mills .................... A61B 5/0404 600/510 |
| 5,391,199 A | | 2/1995 | Ben-Haim |
| 5,443,489 A | | 8/1995 | Ben-Haim |

(Continued)

OTHER PUBLICATIONS

European Search Report for corresponding EPA No. 18180804.9 dated Nov. 7, 2018.

*Primary Examiner* — Glenford J Madamba

(57) ABSTRACT

A console may receive signals from one or more components of the medical system over an input/out (I/O) interface. The console may process the received signals into one or more packets and transmit the one or more packets over a first interface. The console may identify an origin of the one or more packets. The console may monitor time intervals between the one or more packets to determine a connection status of the one or more components. The console may parse each of the one or more packets into a packet header and data and inspect the data for errors. The console may transmit an indication of the connection status and an indication of errors to a display over a second interface. The display may indicate the connection status and the presence of errors using one or more display schemes.

22 Claims, 6 Drawing Sheets

(51) Int. Cl.
*A61B 5/06* (2006.01)
*A61B 5/042* (2006.01)

(56) References Cited

U.S. PATENT DOCUMENTS

| | | |
|---|---|---|
| 5,558,091 A | 9/1996 | Acker et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,266,551 B1 | 7/2001 | Osadchy et al. |
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 7,729,742 B2 | 6/2010 | Govari |
| 9,089,254 B2 | 7/2015 | Govari |
| 9,241,632 B2 | 1/2016 | Kilim et al. |
| 9,241,656 B2 | 1/2016 | Govari et al. |
| 9,498,147 B2 | 11/2016 | Massarwa et al. |
| 2004/0225948 A1* | 11/2004 | Adkisson ............ G06F 11/0724 714/776 |
| 2009/0093806 A1 | 4/2009 | Govari et al. |
| 2009/0118591 A1* | 5/2009 | Kim ..................... A61B 5/0002 600/300 |
| 2009/0138007 A1 | 5/2009 | Govari et al. |
| 2012/0226771 A1* | 9/2012 | Harrington .......... G06F 19/3418 709/217 |
| 2013/0191513 A1* | 7/2013 | Kamen ................... H04L 67/02 709/219 |
| 2013/0347103 A1 | 12/2013 | Veteikis |
| 2014/0188133 A1 | 7/2014 | Misener et al. |
| 2015/0016274 A1 | 1/2015 | Holland |
| 2015/0055573 A1* | 2/2015 | Miklos .................. H04W 76/38 370/329 |
| 2015/0073340 A1 | 3/2015 | Pacheco et al. |
| 2015/0156077 A1* | 6/2015 | Gao .................... H04L 41/0853 709/223 |
| 2015/0373167 A1* | 12/2015 | Murashov ............ H04L 69/321 370/392 |
| 2016/0082243 A1 | 3/2016 | Genstler et al. |

\* cited by examiner

NETWORK SNIFFER FOR SYSTEM WATCHDOG AND DIAGNOSTIC

SUMMARY

Embodiments include methods, systems, and apparatuses for monitoring components of a medical system that provides real-time position and orientation information of a radiofrequency (RF) ablation catheter within a patient's heart. A console may receive signals from one or more components of the medical system over an input/out (I/O) interface. The console may process the received signals into one or more packets and transmit the one or more packets to a system bus over a first interface. The listener may monitor the system bus for the one or more packets. The listener may identify an origin of the one or more packets. The listener may monitor time intervals between the one or more packets to determine a connection status of the one or more components. The listener may parse each of the one or more packets into a packet header and data and inspect the data for errors. The listener may transmit an indication of the connection status and an indication of errors to a display over a second interface. The display may indicate the connection status and the presence of errors using one or more display schemes.

BRIEF DESCRIPTION OF THE DRAWINGS

A more detailed understanding may be had from the following description, given by way of example in conjunction with the accompanying drawings wherein.

DETAILED DESCRIPTION

Figure 1:
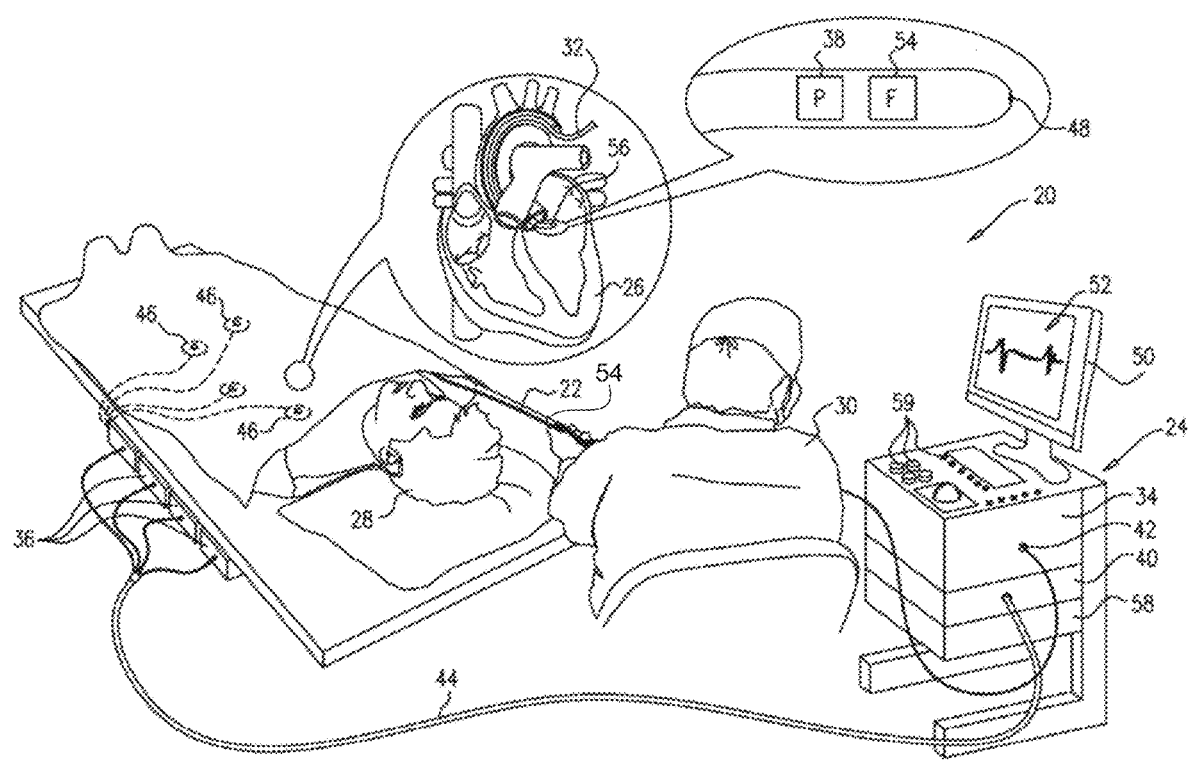
FIG. 1 is a schematic, pictorial illustration of a medical system configured to display an enhanced electrocardiography (ECG) chart, in accordance with an embodiment of the present invention.

Documents incorporated by reference in the present patent application may include terms that are defined in a manner that conflict with the definitions made explicitly or implicitly in the present specification. In the event of any conflicts, the definitions in the present specification should be considered to be controlling.

The present invention relates generally to cardiac electrophysiology, and more specifically to methods, systems, and apparatuses for monitoring components of a medical system that provides real-time position and orientation information of a radiofrequency (RF) ablation catheter within a patient's heart.

During a medical procedure, such as cardiac ablation, there are typically simultaneous streams of real-time data that an operator (e.g., a physician) monitors while performing the procedure. For example, while using an intracardiac catheter to perform an ablation on cardiac tissue, the operator may require real-time electrophysiological (EP) data such as electrocardiography (ECG) data, and ancillary data such as locations of the catheter's distal tip and ablation energy being delivered to the cardiac tissue. The operator may monitor an electrocardiography (ECG) signal collected by body surface sensors and/or intercardiac sensors, as well as ancillary data gathered from one or more devices in real-time. The ancillary data may include measurements received from a distal end of an intracardiac catheter within a cardiac chamber. Examples of these measurements include, but are not limited to, force, tissue proximity to the distal end of the catheter, temperature of cardiac tissue, positions of the distal end of the catheter, respiration indicators, ventricular endocardial local activation time (LAT) values, and measurements of ablation energy delivered by the distal end of the catheter to the cardiac tissue.

Upon collecting first data samples of electrical potentials produced by a heart at a sequence of sampling times, the first data samples may be presented as a chart on a display. The chart may be a trace of the electrical potentials collected at the sampling times. In addition to collecting the first data, second data samples of ancillary data may also be collected at the sampling times or may be calculated from the first data samples. The second data may be presented in the chart, on the display, or by other means.

Systems for performing these medical procedures may include one or more indicators that an individual component is malfunctioning or is disconnected. These indicators are typically based on electrical feedback gathered from the component, and may provide limited information, such as connection status as connected or disconnected.

It may be advantageous to utilize a monitor, for example a network sniffer that operates on a central location to provide information on system status. The network sniffer may operate on a system bus of a console controlling the medical procedure and may provide information on system status, sources of failure, an unplugged device, and/or a hardware malfunction within a device connected to the console. Examples of a network sniffer for analyzing data on a system bus to monitor the status of a medical system are described herein.

Referring now to FIG. 1, an illustration of a medical system 20 that may be used to generate and display a chart 52 is shown. The system 20 may include a probe 22, such as an intracardiac catheter, and a console 24. As described herein, the probe 22 is used for diagnostic or therapeutic treatment, such as for mapping electrical potentials in a heart 26 of a patient 28. Alternatively, the probe 22 may be used, mutatis mutandis, for other therapeutic and/or diagnostic purposes in the heart, lungs, or in other body organs and ear, nose, and throat (ENT) procedures.

An operator 30 may insert the probe 22 into the vascular system of the patient 28 so that a distal end 32 of the probe 22 enters a chamber of the patient's heart 26. The console 24 may use magnetic position sensing to determine position coordinates of the distal end 32 inside the heart 26. To determine the position coordinates, a driver circuit 34 in the console 24 may drive field generators 36 to generate magnetic fields within the body of the patient 28. The field generators 36 may include coils that may be placed below the torso of the patient 28 at known positions external to the patient 28. The coils may generate magnetic fields in a predefined working volume that contains the heart 26.

A location sensor 38 within the distal end 32 of probe 22 may generate electrical signals in response to these magnetic fields. A signal processor 40 may process these signals in order to determine the position coordinates of the distal end 32, including both location and orientation coordinates. The method of position sensing described hereinabove is implemented in the CARTO™ mapping system produced by Biosense Webster Inc., of Diamond Bar, Calif., and is described in detail in the patents and the patent applications cited herein.

The location sensor 38 may transmit a signal to the console 24 that is indicative of the location coordinates of the distal end 32. The location sensor 38 may include one or more miniature coils oriented along different axes. Alternatively, the location sensor 38 may include another type of magnetic sensor or position transducers of other types, such as impedance-based or ultrasonic location sensors. Although FIG. 1 shows the probe 22 with a single location sensor 38, embodiments of the present invention may utilize probes without a location sensor 38 and probes with more than one location sensor 38.

The probe 22 may also include a force sensor 54 contained within the distal end 32. The force sensor 54 may measure a force applied by the distal end 32 to the cardiac tissue of the heart 26 and generating a signal that is sent to the console 24. The force sensor 54 may include a magnetic field transmitter and a receiver connected by a spring in the distal end 32, and may generate an indication of the force based on measuring a deflection of the spring. Further details of this sort of probe and force sensor are described in U.S. Patent Application Publications 2009/0093806 and 2009/0138007, whose disclosures are incorporated herein by reference. Alternatively, the distal end 32 may include another type of force sensor that uses, for example, fiber optics or impedance measurements.

The probe 22 may include an electrode 48 coupled to the distal end 32 and configured to function as an impedance-based position transducer. Additionally or alternatively, the electrode 48 may be configured to measure a certain physiological property, for example the local surface electrical potential of the cardiac tissue at one or more of the multiple locations. The electrode 48 may be configured to apply radio frequency (RF) energy to ablate cardiac tissue in the heart 26.

Although the example medical system 20 may be configured to measure the position of the distal end 32 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499, and 6,177,792, whose disclosures are incorporated herein by reference. Impedance-based position tracking techniques are described, for example, in U.S. Pat. Nos. 5,983,126, 6,456,864 and 5,944,022, whose disclosures are incorporated herein by reference.

The signal processor 40 may be included in a general-purpose computer, with a suitable front end and interface circuits for receiving signals from the probe 22 and controlling the other components of the console 24. The signal processor 40 may be programmed, using software, to carry out the functions that are described herein. The software may be downloaded a memory device of the console 24 in electronic form, over a network, for example, or it may be provided on non-transitory tangible media, such as optical, magnetic or electronic memory media. Alternatively, some or all of the functions of the signal processor 40 may be performed by dedicated or programmable digital hardware components.

In the example of FIG. 1, the console 24 may also be connected by a cable 44 to external sensors 46. The external sensors 46 may include body surface electrodes and/or position sensors that may be attached to the patient's skin using, for example, adhesive patches. The body surface electrodes may detect electrical impulses generated by the polarization and depolarization of cardiac tissue. The position sensors may use advanced catheter location and/or magnetic location sensors to locate the probe 22 during use. Although not shown in FIG. 1, the external sensors 46 may be embedded in a vest that is configured to be worn by the patient 28. The external sensors 46 may help identify and track the respiration cycle of the patient 28. The external sensors 46 may transmit information to the console 24 via the cable 44.

Additionally, or alternatively, the probe 22, and the external sensors 46 may communicate with the console 24 and one another via a wireless interface. For example, U.S. Pat. No. 6,266,551, whose disclosure is incorporated herein by reference, describes, inter alia, a wireless catheter, which is not physically connected to signal processing and/or computing apparatus. Rather, a transmitter/receiver is attached to the proximal end of the catheter. The transmitter/receiver communicates with a signal processing and/or computer apparatus using wireless communication methods, such as infrared (IR), radio frequency (RF), wireless, Bluetooth, or acoustic transmissions.

The probe 22 may be equipped with a wireless digital interface that communicates with a corresponding input/output (I/O) interface 42 in the console 24. The wireless digital interface and the I/O interface 42 may operate in accordance with any suitable wireless communication standard that is known in the art, such as IR, RF, Bluetooth, one or more of the IEEE 802.11 families of standards, or the HiperLAN standard. The external sensors 46 may include one or more wireless sensor nodes integrated on a flexible substrate. The one or more wireless sensor nodes may include a wireless transmit/receive unit (WTRU) enabling local digital signal processing, a radio link, and a power supply such as a rechargeable battery.

The I/O interface 42 may enable the console 24 to interact with the probe 22 and the external sensors 46. Based on the electrical impulses received from the external sensors 46 and signals received from the probe 22 via the I/O interface 42 and other components of the medical system 20, the signal processor 40 may generate the chart 52 to be shown on a display 50.

During the diagnostic treatment, the signal processor 40 may generate the chart 52 and store data representing the chart 52 in a memory 58. The memory 58 may include any suitable volatile and/or non-volatile memory, such as random access memory or a hard disk drive. The operator 30 may be able to manipulate the chart 52 using one or more input devices 59. Alternatively, the medical system 20 may include a second operator that manipulates the console 24 while the operator 30 manipulates the probe 22.

It should be noted that the configuration shown in FIG. 1 is exemplary. Any suitable configuration of the medical system 20 may be used and implemented.

Figure 2:
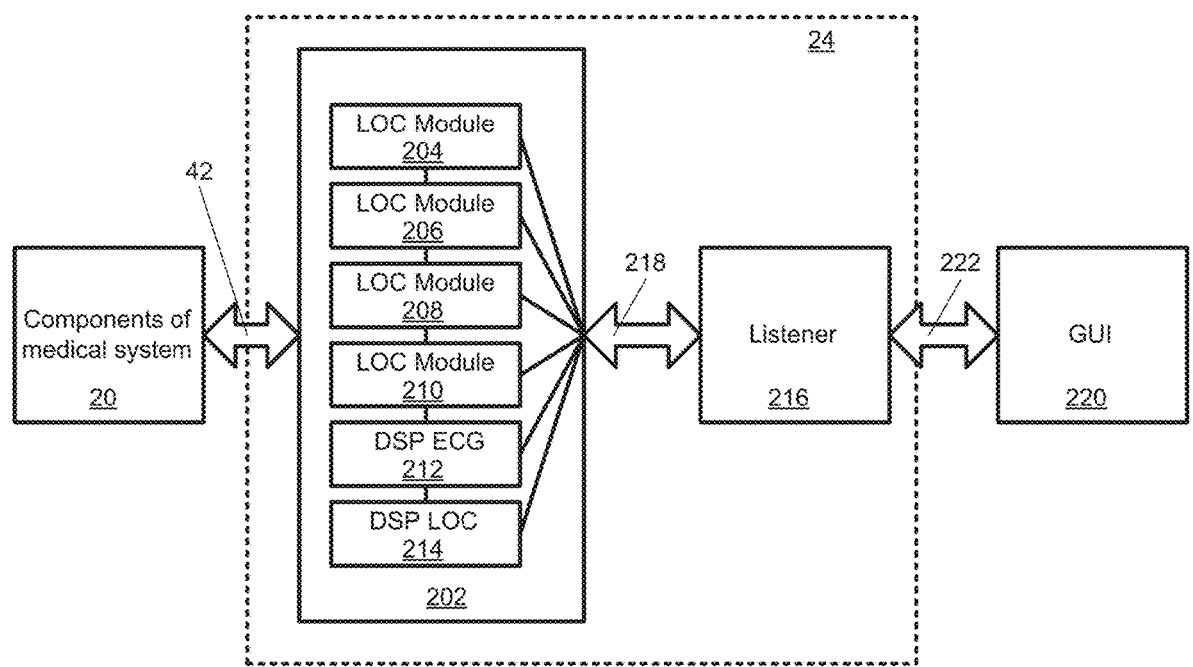
FIG. 2 is a diagram illustrating components of a console used in the medical system.

Referring now to FIG. 2, a diagram illustrating elements of the console 24 is shown. The I/O interface 42 may direct inputs from the probe 22 and the external sensors 46 to a module bank 202 in the console 24. The module bank 202 may be consistent with different configurations of the medical system 20. For example, the module bank 202 may include one or more location (LOC) modules, such as, for example LOC Module 204, LOC module 206, LOC module 208, and LOC Module 210. The LOC modules may include one or more processors that acquire analog signals from one or more of the probe 22 and the external sensors 46 and amplify, filter, and convert the analog signals to a digital data stream. Alternatively, if the probe 22 and the external sensors 46 communicate with the console 24 via a wireless digital interface, the LOC modules may receive the digital information via the I/O interface 42 directly. The LOC modules may be connected to one or more probes 22.

The module bank 202 may also include a digital signal processing (DSP) ECG module 212. The DSP ECG module 212 may include one or more processors that perform noise reduction on digital signals from the one or more of the probe 22 and the external sensors 46 used to generate the chart 52. The DSP ECG module 212 may perform line noise rejection. The line noise rejection process may use an algorithm that defines a frequency and amplitude of a noise signal and subtracts this signal from the received digital signals. The DSP ECG module 212 may include a low pass filter and a high pass filter to filter noise from the digital signals. The low pass filter and the high pass filter may be infinite impulse response (IIR) filters. The DSP ECG module 212 may perform data rate decimation and filter control using finite impulse response (FIR) filters.

The module bank 202 may also include a DSP LOC module 214. The DSP LOC module 214 may include one or more processors that determine the position of the probe 22 based on the processed signals from one or more of the probe 22 and the external sensors 46. The DSP LOC module 214 may correct the processed signals from one or more of the probe 22 and the external sensors 46 based on probe 22 calibration data.

The modules may communicate with a listener 216 over a first interface 218. The first interface 218 may use transmission control protocol/internet protocol (TCP/IP) to communicate with the listener 216. TCP/IP is a connection-oriented protocol that may require handshaking to set up end-to-end communications. Once a connection is established, data may be sent bi-directionally over the connection. The TCP/IP may manage message acknowledgment, retransmission and timeout. Multiple attempts to deliver a message may be made. If the message gets lost along the way, the destination device may re-request the lost part. In the case of multiple timeouts, the connection may be dropped.

If two messages are sent over a connection in sequence, the first message may reach the receiving application first. When data segments arrive in the wrong order, TCP/IP buffers may delay the out-of-order data until all data can be properly re-ordered and delivered to the application. Data may be read as a byte stream and no distinguishing indications may be transmitted to signal message (segment) boundaries.

In TCP/IP, higher layers manage the assembling of a message or data into smaller packets that are transmitted over a communications interface, such as the first interface 218. The smaller packets may be reassembled by higher layers of a destination device into the original message or data. The lower IP layer handles the address part of each packet so that it gets to the right destination. Devices may check the IP address to see where the packets are to be forwarded. Even though some packets from the same message may be routed differently than others, they may be reassembled at the destination. Each of the modules of the module bank 202 may have unique IP addresses and one or more ports. In addition, if one or more of the probe 22 and the external sensors 46 communicate with the console 24 via a wireless interface, the probe 22 and the external sensors 46 may also have unique IP addresses.

The module bank 202 may send data received from the probe 22 and the external sensors 46 over the first interface 218 as data packets. The listener 216 may include one or more processors located on and/or configured to operate on a system bus in the console 24. The system bus may be a computer bus, including one or more hardware components and software, that connects the major components of a computer system such as the console 24. The system bus may combine the functions of a data bus to carry information, an address bus to determine where the information should be sent, and a control bus to determine its operation. The control bus may carry control, timing, and coordination signals to manage the various functions across the medical system 20. The address bus may be used to specify memory locations for the data being transferred. The data bus, which may be a bidirectional path, carries the actual data between the processor, the memory and the peripherals.

The system bus may connect a central processing unit (CPU) with a main memory and, in some examples, with a level 2 (L2) cache. Other buses, such as I/O buses, may branch off from the system bus to provide a communication channel between the CPU and the other peripherals. Components of the medical system 20 may be connected to the system bus via an Ethernet switch.

The listener 216 may allow for monitoring and feedback of the status of the medical system 20. The listener 216 may monitor the system bus of the console 24 to determine the status of each component in the medical system 20 including, for example, one or more of the probe 22, the external sensors 46, and the modules of the module bank 202. Examples of statuses that may be determined include, but are not limited to: whether a component is connected to a network, the voltage integrity of a component, whether or not a component passes a self-test, and whether or not the component is connected to the console 24. The listener 216 may detect whether the medical system 20 is set up correctly and which components are connected.

The listener 216 may be configured with the IP addresses of the monitored network components. The probe 22 and the one or more external sensors 46 may have a type ID, but it may not be unique for each device. However, a module ID may be unique, and it can be determined which of the probe 22 and the one or more external sensors 46 are connected to specific module based on the combined module ID and device type ID. In other words, modules connected through the first interface 218 may have unique ID and devices connected to modules via the I/O interface 42 may provide information about device type, calibration, serial number etc. Each device may be connected to different modules.

The IP addresses may be defined in a text initialization file. The listener 216 may monitor time intervals between data packet transmissions between different parts of the network. For example, the listener 216 may monitor the frequency of sending update messages to the GUI 220. The listener 216 may monitor a communication timeout duration between a component and the console 24 that indicates a disconnection of the component. The communication timeout may be defined in the text initialization file.

The listener 216 may provide information to the GUI 220 over a second interface 222. Although the GUI 220 is shown separately from the console 24, it may be located on the console 24 with the module bank 202. The listener 216 may periodically send messages to the GUI 220, for example, every second. The second interface 222 may use TCP/IP. Alternatively, the second interface 222 may use the user datagram protocol (UDP).

As compared to TCP/IP, the UDP is a simpler message-based connectionless protocol. Connectionless protocols may not set up a dedicated end-to-end connection. Information may be transmitted in one direction from source to destination without verifying the readiness or state of the receiver. When a UDP message is sent, it cannot be known if it will reach its destination. In UDP there is no concept of acknowledgment, retransmission, or timeout. If two messages are sent to the same recipient, the order in which they arrive may not be predictable. The UDP may not order messages or track connections. The UDP may be a small transport layer designed on top of IP.

In UDP, packets may be sent individually and may be checked for integrity only if they arrive. A read operation at the receiver may yield an entire message as it was originally sent. Because it is connectionless, the UDP can broadcast (i.e., sent packets may be addressed to be receivable by all devices on a subnet). This may allow the GUI 220 to run on multiple devices at once.

Figure 3:
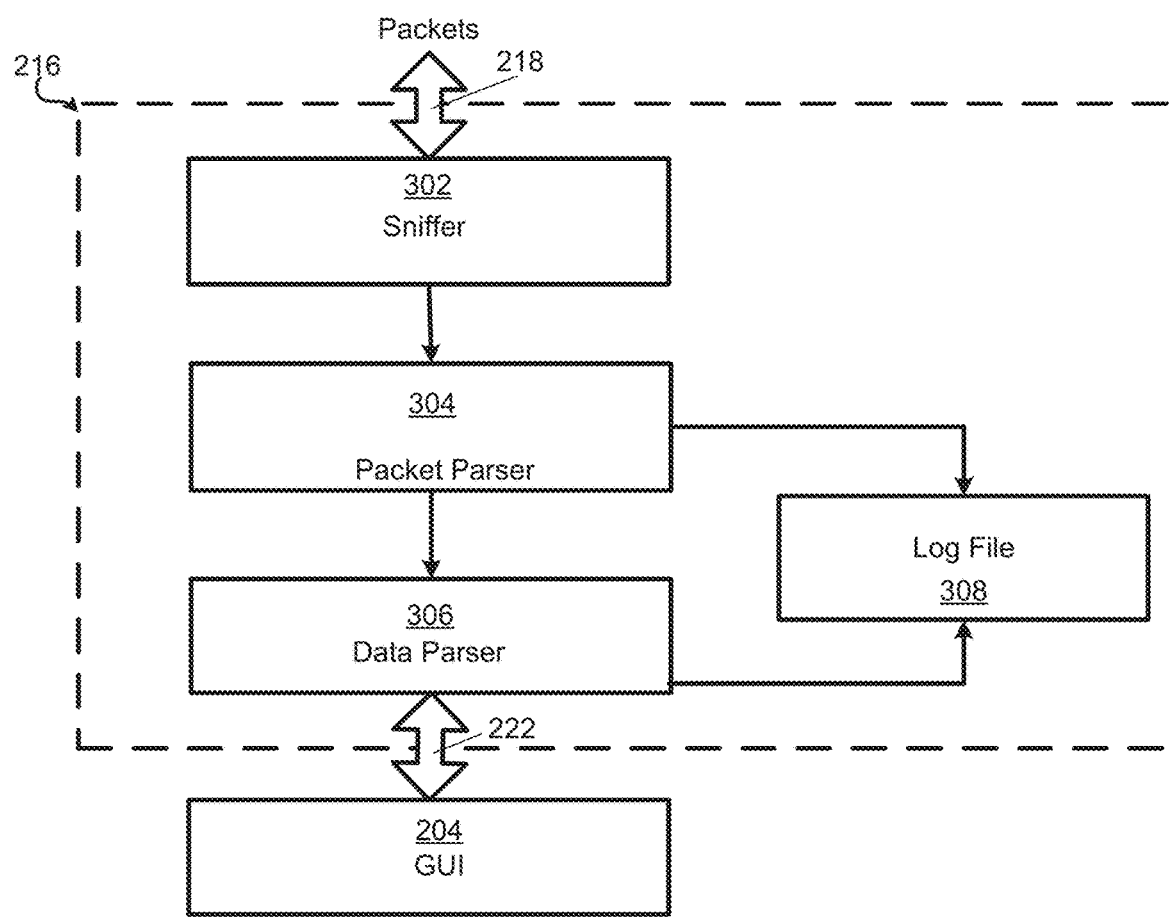
FIG. 3 is a diagram illustrating elements of the listener that may operate on a system bus of the console.

Referring now to FIG. 3, a diagram illustrating elements of the listener 216 is shown. The listener 216 may include a sniffer module 302. The sniffer module 302 may monitor the system bus for packets from the module bank 202. As described above, each component of the network may have its own IP address. The sniffer module 302 may identify packets from the module bank 202 based on the IP address and/or port settings found in a packet header, which may be unique to each component. The sniffer module 302 may allow the listener 216 to monitor the time intervals between data packet transmissions from the module bank 202.

The sniffer module 302 may send the packets from the module bank 202 to a packet parser 304, which may parse the packets into the packet header and the data. The packet parser 304 may filter packets containing unusable data. The packet parser 304 may also write the packet header (e.g., TCP header) information to a log file 308. The log file may be used to analyze temporal events and potential sequence errors that may cause a failure. The packet parser 304 may send the data to a data parser 306. The data parser 306 may parse the data and write details about component failures and connection changes to the log file 308. The data parser 306 may send commands to the GUI 220 based on the parsed data.

Figure 4:
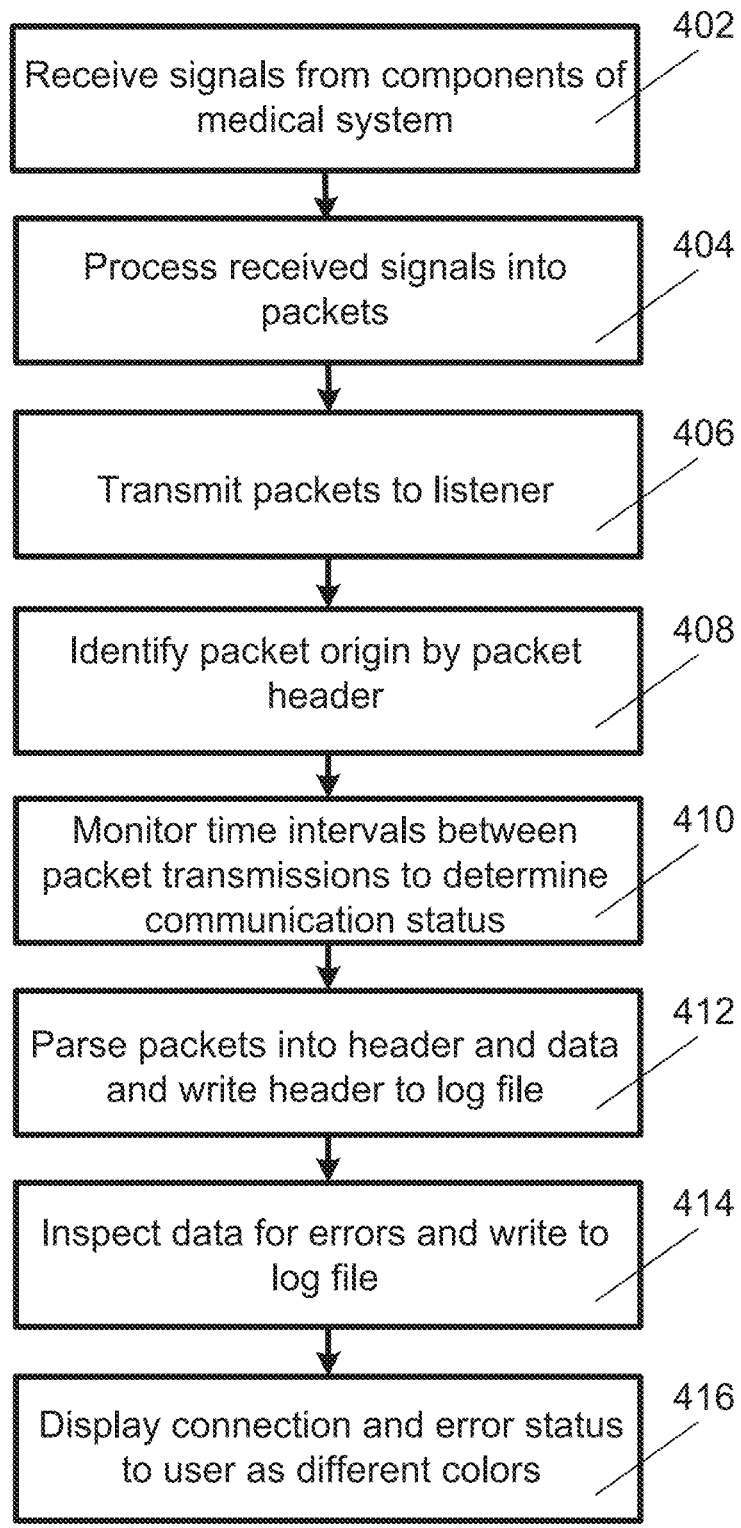
FIG. 4 is a flowchart illustrating the network sniffing process.

Referring now to FIG. 4, a flowchart illustrating the network sniffing process is shown. In step 402, the module bank 202 may receive signals from components of the system. The signals may be transmitted from the probe 22 and the external sensors 46 over the I/O interface 42. The received signals may be analog signals from one or more of the probe 22 and the external sensors 46. Alternatively, the received signals may be digital signals received over a wireless interface.

In step 404, if the received signals are analog signals from one or more of the probe 22 and the external sensors 46, the received signals may be amplified, filtered, and transformed to a digital data stream. As described above, one or more noise reduction and filtering processes may be performed on the digital data stream, or alternatively, the received digital signals.

In step 406, the digital data stream may be transmitted to the listener 216 as data packets over the first interface 218 as described above.

In step 408, the sniffer 302 may identify the origin of individual packets using IP address and port information associated with components of the medical system 20, which may be found in the packet headers.

In step 410, the sniffer 302 may monitor time intervals between data packet transmissions between different parts of the network. The listener 216 may use a predetermined time interval to determine if there is a connection timeout (i.e., a component is disconnected).

In step 412, the packet parser 304 may parse the packets into the packet header and the data. The packet parser 304 may filter packets containing unusable data. The packet parser 304 may also write the packet header information to the log file 308.

In step 414, the data parser 306 may parse the data for error flags. The data parser 306 may write details about component failures and connection changes to the log file 308.

In step 416, the listener 216 may provide information about connection timeouts and errors related to specific system components to the GUI 220 over the second interface 222. It should be noted that although the steps in FIG. 4 are shown in a particular sequence, they may be performed in any order.

Figure 5:
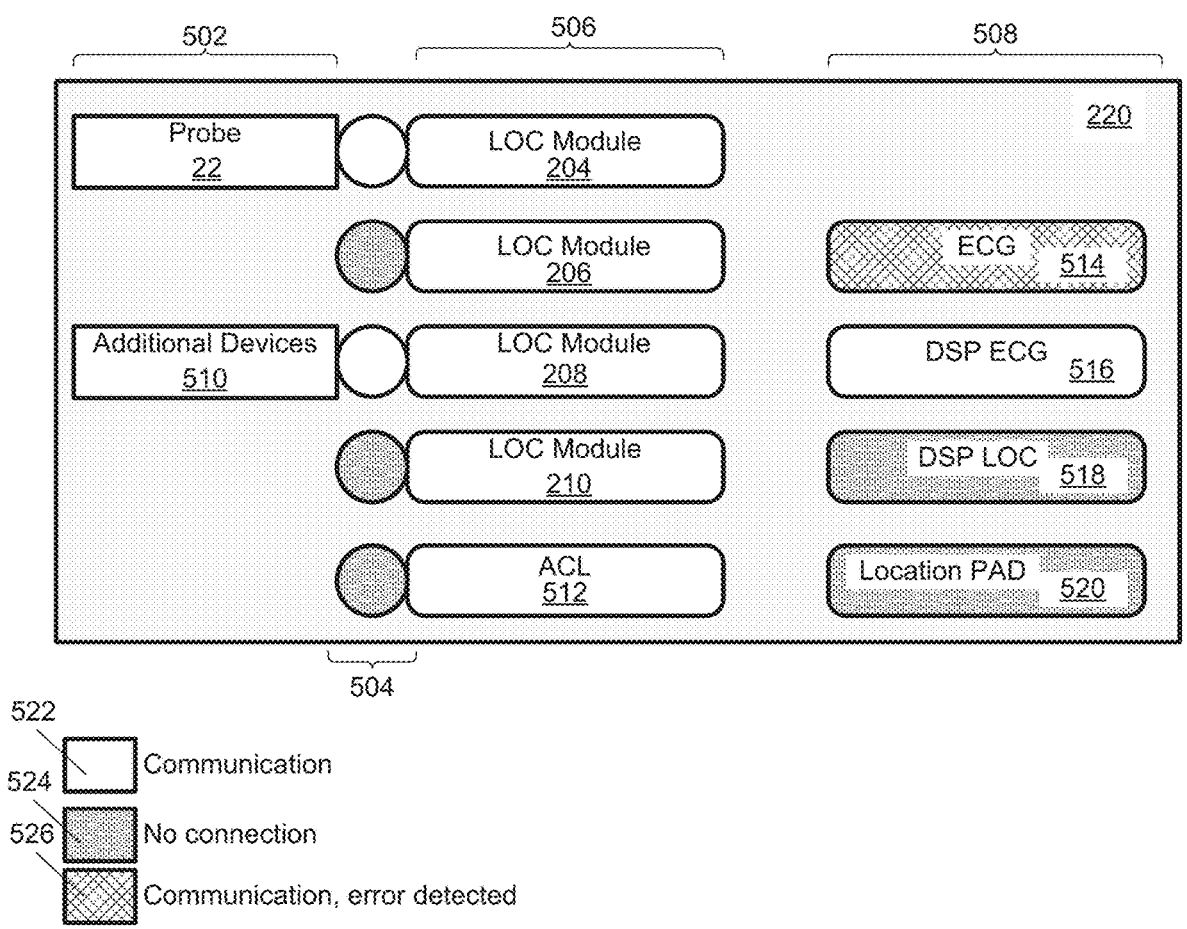
FIG. 5 is a diagram illustrating information from the listener that may be displayed on a graphical user interface (GUI)

Referring now to FIG. 5, a diagram illustrating information received from the listener 216 that may be displayed by the GUI 220 is shown. One or more elements of the medical system 20 may be represented on the GUI 220. For example, the GUI 220 may show a device status 502, a device connection status 504, a module status 506, and a display status 508. The device status 502 may include any device in the medical system, such as one or more of the probe 22, the external sensors 46, and one or more additional devices 510. The module status 506 may include any module in the medical system 20, such as, but not limited to the module bank 202 described above with reference to FIG. 2. The module status 506 may include the LOC module 204, LOC module 206, LOC module 208, LOC module 210, and an advanced current location (ACL) module 512. The ACL module 512 may be used to determine the position of the probe 22 based on received current values from one or more of the position sensors in the external sensors 46. The display status 508 may include any component in the medical system 20 used to display information to the operator 30, such as, but limited to an ECG 514, DSP ECG 516, DSP LOC 518, and Location PAD 520.

One or more display schemes based on the information received from the listener 216 may be used to indicate the status of each element. The one or more display schemes may include, for example, illumination patterns, shapes, audio feedback, haptic feedback, or a color coding scheme that may be displayed to the operator 30. The one or more display schemes may be presented individually or in combination with additional schemes. The one or more display schemes may indicate that there is communication with a component with no errors, there is no connection with a component, or that there is communication with a component with errors.

The color coding scheme may indicate whether there is communication with a component with no errors by using a first color 522, such as the color green. For example, if the DSP ECG module 516 is colored green as in FIG. 5, the module may be connected to the network and may be sending packets within the defined time intervals. The GUI 220 may indicate that there is communication with the element 522 if a communication from the element is received within a predetermined time period, which may be defined in seconds or fractions of a second. The predetermined time may be the same for every element or may be different for each element.

The color coding scheme may indicate whether there is no connection with a component by using a second color 524, such as the color grey. For example, if the DSP LOC module 518 is colored grey as in FIG. 5, it may not be connected to the network. The module may have been manually disconnected from the network, the module have a failure, or the module may not be receiving power. The GUI 220 may indicate that there is no connection with the component if a communication is not received within the predetermined time period. Additionally or alternatively, an audio or haptic signal may be presented to the operator 30 to indicate there is no connection with the component. The audio or haptic signal may be generated by the console 24 or it may be produced by one or more of the probe 22 and the external sensors 46.

The color coding scheme may indicate whether there is communication with a component but an error is detected by using a third color 526, such as the color red. For example, if the ECG module 514 is colored red as in FIG. 5, the listener 216 may have determined that there a data packet is missing from the system bus or that there is unusable data within a packet. The GUI 220 may indicate that there is communication with an element but an error is detected if, for example, the data parser 306 detects an error flag in the parsed data of a packet. Additionally or alternatively, an audio or haptic signal may be presented to the operator 30 to indicate there is communication with a component but an error is detected. The audio or haptic signal may be generated by the console 24 or it may be produced by one or more of the probe 22 and the external sensors 46. The audio or haptic signal indicating an error may be the same or may be different than the audio or haptic signal indicating a disconnection.

As shown in FIG. 5, the GUI 220 may show that the probe 22 is communicating without any detected problems, that it is connected to the LOC Module 204 without any detected problems, and that the LOC Module 204 is communicating without any detected problems. The GUI 220 may show that that LOC Module 206 is communicating properly, but that there is no connection to a peripheral device as shown by the connection status 504. The LOC Module 206 may be functioning properly and is available to attach a peripheral device. In addition, the GUI 220 may show that the ECG module 514 is communicating, but that there is an error in the element. The error may be part of the message in a data packet transmitted by the ECG module 514. The error may indicate, for example, missing data from one or more of the probe 22 and the external sensors 46 or a module self-test failure.

Figure 6:
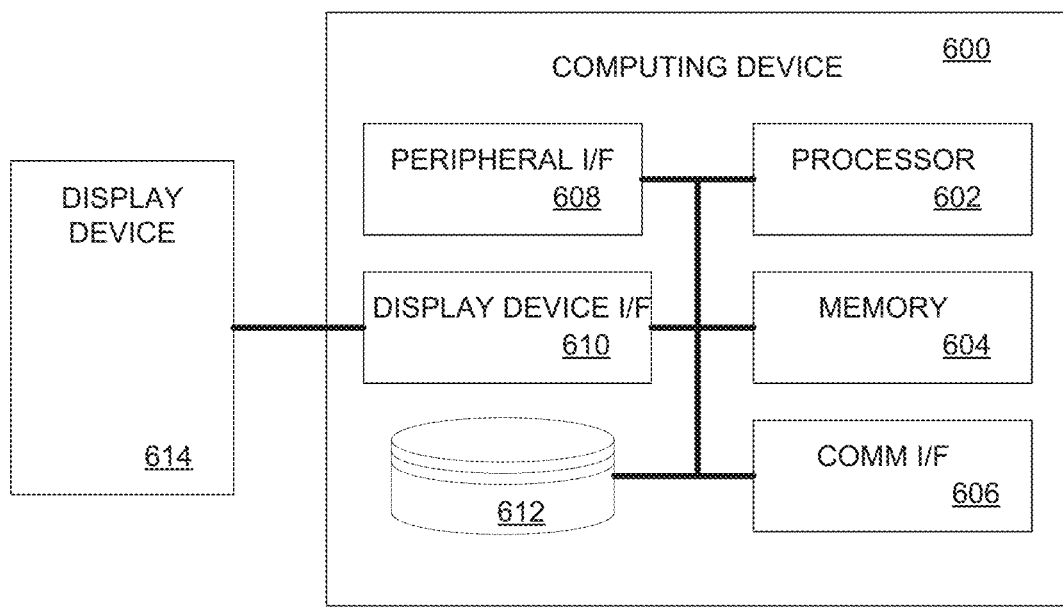
FIG. 6 is an example computing device that may be used to implement features described below.

Referring now to FIG. 6, an example computing device 600 that may be used to implement features of the elements described above is shown. The computing device 600 may be part of the console 24 as described above with reference to FIG. 1. The computing device 600 may include a processor 602, a memory device 604, a communication interface 606, a peripheral device interface 608, a display device interface 610, and a storage device 612. FIG. 6 also shows a display device 614, which may be coupled to or included within the computing device 600.

The memory device 604 may be, or may include, a device such as a Dynamic Random Access Memory (D-RAM), Static RAM (S-RAM), or other RAM or a flash memory. The storage device 612 may be, or may include, a hard disk, a magneto-optical medium, an optical medium such as a CD-ROM, a digital versatile disk (DVDs), or Blu-Ray disc (BD), or other type of device for electronic data storage.

The communication interface 606 may be, for example, a communications port, a wired transceiver, a wireless transceiver, and/or a network card. The communication interface 606 may be capable of communicating using technologies such as Ethernet, fiber optics, microwave, xDSL (Digital Subscriber Line), Wireless Local Area Network (WLAN) technology, wireless cellular technology, and/or any other appropriate technology.

The peripheral device interface 608 may be an interface configured to communicate with one or more peripheral devices. The peripheral device interface 608 may operate using a technology such as Universal Serial Bus (USB), PS/2, Bluetooth, infrared, serial port, parallel port, and/or other appropriate technology. The peripheral device interface 608 may, for example, receive input data from an input device such as a keyboard, a mouse, a trackball, a touch screen, a touch pad, a stylus pad, and/or other device. Alternatively or additionally, the peripheral device interface 608 may communicate output data to a printer that is attached to the computing device 600 via the peripheral device interface 608.

The display device interface 610 may be an interface configured to communicate data to display device 1014. The display device 1014 may be, for example, a monitor or television display, a plasma display, a liquid crystal display (LCD), and/or a display based on a technology such as front or rear projection, light emitting diodes (LEDs), organic light-emitting diodes (OLEDs), or Digital Light Processing (DLP). The display device interface 610 may operate using technology such as Video Graphics Array (VGA), Super VGA (S-VGA), Digital Visual Interface (DVI), High-Definition Multimedia Interface (HDMI), or other appropriate technology. The display device interface 610 may communicate display data from the processor 602 to the display device 614 for display by the display device 614. As shown in FIG. 6, the display device 614 may be external to the computing device 600, and coupled to the computing device 600 via the display device interface 610. Alternatively, the display device 614 may be included in the computing device 600.

An instance of the computing device 600 of FIG. 6 may be configured to perform any feature or any combination of features described above. In such an instance, the memory device 604 and/or the storage device 612 may store instructions which, when executed by the processor 602, cause the processor 602 to perform any feature or any combination of features described above. Alternatively or additionally, in such an instance, each or any of the features described above may be performed by the processor 602 in conjunction with the memory device 604, communication interface 606, peripheral device interface 608, display device interface 610, and/or storage device 612.

Although FIG. 6 shows that the computing device 600 includes a single processor 602, single memory device 604, single communication interface 606, single peripheral device interface 608, single display device interface 610, and single storage device 612, the computing device may include multiples of each or any combination of these components 602, 604, 606, 608, 610, 612, and may be configured to perform, mutatis mutandis, analogous functionality to that described above.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for use in a medical system, the method comprising:
   supplying a medical system arranged to provide position and orientation information of an ablation catheter within cardiac tissue of a patient, the medical system including one or more components comprising
      a probe having a distal end and arranged for insertion in the vascular system of a patient;
      a location sensor disposed on the probe, the location sensor arranged to transmit signals indicative of the position and orientation of the probe within a patient's heart;
      a force sensor disposed on the probe and arranged to transmit signals indicative of a force applied by the probe to cardiac tissue;
      an electrode coupled to the distal end of the probe configured to ablate cardiac tissue in the heart;
      one or more external sensors on a patient's body and arranged to transmit signals indicative of the position and orientation of the probe within the patient's heart and indicative of electrical impulses generated by cardiac tissue;
   receiving processed signals from the one or more components of the medical system, at one or more unique modules, each component having a type ID and each unique module having a module ID, wherein each unique module receives data from a single component of the one or more components;
generating one or more packets by the one or more unique modules based on the received processed signals;
monitoring a system bus for the one or more packets received over a first interface from a plurality of the one or more unique modules;
   identifying an origin of the one or more packets based on a combination of the type ID and the module ID corresponding to the one or more packets;
   monitoring time intervals between the one or more packets from a first module of the one or more modules to determine a connection status of the one or more components;
   parsing each of the one or more packets into a packet header and data;
   inspecting the data for errors;
   transmitting an indication of the connection status and an indication of errors to a display over a second interface.

2. The method of claim 1, wherein the signals comprise real-time position and orientation information of the probe.

3. The method of claim 1, wherein the signals comprise electrocardiography (ECG) information from the one or more external sensors on a patient's body.

4. The method of claim 1, further comprising:
   receiving analog signals from the one or more components of the medical system over an input/output (I/O) interface; and
   converting the analog signals into digital signals to form the processed signals.

5. The method of claim 4, further comprising:
   performing signal noise reduction on the digital signals using one or more filters.

6. The method of claim 1, wherein the first interface comprises a transmission control protocol/internet protocol (TCP/IP) interface.

7. The method of claim 1, wherein the identifying the origin of the one or more packets comprises determining a source IP address in a header of the one or more packets.

8. The method of claim 1, wherein the connection status is determined by comparing the time intervals between the one or more packets with a predetermined time interval indicating a connection timeout.

9. The method of claim 1, further comprising:
   storing the packet header and the errors in a log file.

10. The method of claim 1, wherein the indication of the connection status and the indication of errors are displayed using a color coding scheme comprising:
   a first color indicating there is communication with a component of the one or more components with no errors;
   a second color indicating there is no communication with a component of the one or more components; and
   a third color indicating there is communication with a component of the one or more components with one or more errors.

11. The method of claim 1, wherein the probe is arranged for mapping electrical potential of cardiac tissue of a patient.

12. The method of claim 1, additionally comprising monitoring the system bus to determine the voltage integrity of the one or more components.

13. A device for use in combination with a medical system that provides position and orientation information of an ablation catheter within a patient's heart, the medical system comprising:
   one or more components including;
      a probe having a distal end and arranged for insertion in the vascular system of a patient;
      a location sensor disposed on each of the probe, the location sensor arranged to transmit signals indicative of the position and orientation of the probe within a patient's heart,
      a force sensor disposed on the probe and arranged to transmit signals indicative of a force applied by the probe to cardiac tissue,
      an electrode coupled to the distal end of the probe configured to ablate cardiac tissue in the heart,
      one or more external sensors situated on a patient's body and arranged to transmit signals indicative of the position and orientation of the probe within the patient's heart and indicative of electrical impulses generated by cardiac tissue;
   the device comprising:
   a console having one or more processors; and
   a non-transitory computer readable medium storing a plurality of instructions, which when executed, cause the one or more processors to:
   receive processed signals from the one or more components of the medical system at one or more unique modules, each component having a type ID and each unique module having a module ID, wherein each unique module receives data from a single component of the one or more components;
   generate one or more packets by the one or more unique modules based on the received processed signals;
   monitor a system bus for one or more packets received over a first interface from a plurality of the one or more unique modules;

identify an origin of the one or more packets based on a combination of the type ID and the module ID corresponding to the one or more packets;

monitor time intervals between the one or more packets from a first module of the one or more modules to determine a connection status of the one or more components;

parse each of the one or more packets into a packet header and data;

inspect the data for errors; and transmit an indication of the connection status and an indication of errors to a display over a second interface.

14. The device of claim 13, wherein the signals comprise real-time position and orientation information of the probe.

15. The device of claim 13, wherein the signals comprise electrocardiography (ECG) information from the one or more external sensors on a patient's body.

16. The device of claim 13, further comprising:

an input/output (I/O) interface coupled to the one or more processors, wherein the I/O interface is configured to receive analog signals from the one or more components of the medical system, and wherein the one or more processors are further configured to convert the analog signals into digital signals to form the processed signals.

17. The device of claim 16, wherein the one or more processors are further configured to perform signal noise reduction on the digital signals using one or more filters.

18. The device of claim 13, wherein the first interface comprises a transmission control protocol/internet protocol (TCP/IP) interface.

19. The device of claim 13, wherein the identifying the origin of the one or more packets comprises determining a source IP address in a header of the one or more packets.

20. The device of claim 13, wherein the connection status is determined by comparing the time intervals between the one or more packets with a predetermined time interval indicating a connection timeout.

21. The device of claim 13, wherein the instructions, when executed, further cause the one or more processors to store the packet header and the errors in a log file.

22. The device of claim 13, wherein the indication of the connection status and the indication of errors are displayed using a color coding scheme comprising:

a first color indicating there is communication with a component of the one or more components with no errors;

a second color indicating there is no communication with a component of the one or more components; and a third color indicating there is communication with a component of the one or more components with one or more errors.

\* \* \* \* \*

UNITED STATES PATENT AND TRADEMARK OFFICE
CERTIFICATE OF CORRECTION

PATENT NO. : 10,874,462 B2
APPLICATION NO. : 15/638690
DATED : December 29, 2020
INVENTOR(S) : Assaf Govari et al.

It is certified that error appears in the above-identified patent and that said Letters Patent is hereby corrected as shown below:

On the Title Page
In Item (57), under "ABSTRACT", in Column 2, Line 2, delete "input/out (I/O)" and insert -- input/output (I/O) --, therefor.

In the Specification
In Column 1, Line 9, delete "radiofrequency" and insert -- radio frequency --, therefor.
In Column 1, Line 11, delete "input/out" and insert -- input/output --, therefor.
In Column 1, Line 60, delete "radiofrequency" and insert -- radio frequency --, therefor.
In Column 9, Line 62, delete "digital versatile disk (DVDs)," and insert -- digital versatile disks (DVDs), --, therefor.

In the Claims
In Column 12, Line 35, in Claim 13, delete "including;" and insert -- including: --, therefor.
In Column 12, Line 37, in Claim 13, delete "patient;" and insert -- patient, --, therefor.

Signed and Sealed this
Twenty-seventh Day of December, 2022

Katherine Kelly Vidal
*Director of the United States Patent and Trademark Office*